United States Patent [19]

Rothman et al.

[11] 4,225,580

[45] Sep. 30, 1980

[54] METHOD FOR CLEANSING FLUID DISCHARGING SKIN SURFACES, WOUNDS AND MUCOUS MEMBRANES AND MEANS FOR CARRYING OUT THE METHOD

[75] Inventors: Ulf S. E. Rothman, Bjärred; Sten A. L. Jacobsson, Malmö, both of Sweden

[73] Assignee: Pharmacia Aktiebolag, Uppsala, Sweden

[21] Appl. No.: 619,148

[22] Filed: Oct. 2, 1975

Related U.S. Application Data

[63] Continuation of Ser. No. 437,558, Jan. 27, 1974, abandoned.

[51] Int. Cl.$^2$ .............................................. A61K 31/74
[52] U.S. Cl. ........................................................ 424/78
[58] Field of Search ................... 424/78, 28, DIG. 13

[56] References Cited

U.S. PATENT DOCUMENTS

| | | | |
|---|---|---|---|
| 2,039,082 | 4/1936 | Jungmann | 424/28 |
| 2,602,042 | 7/1952 | Abbott | 424/28 |
| 2,855,925 | 10/1958 | Novak | 424/28 |
| 3,098,790 | 7/1963 | Mettentleiter | 424/28 |
| 3,238,100 | 3/1966 | Meyer | 424/28 |
| 3,328,259 | 6/1967 | Anderson | 424/28 |
| 3,579,628 | 5/1971 | Gander et al. | 424/28 |
| 3,624,209 | 11/1971 | Granatek et al. | 424/79 |

FOREIGN PATENT DOCUMENTS

| | | | |
|---|---|---|---|
| 974054 | 11/1964 | United Kingdom | 424/78 |
| 1200106 | 7/1970 | United Kingdom | 424/78 |
| 1224009 | 3/1971 | United Kingdom | 424/28 |

*Primary Examiner*—Frederick E. Waddell
*Attorney, Agent, or Firm*—Fred Philpitt

[57] ABSTRACT

The present invention relates to a method and material for cleansing fluid discharging skin surfaces, wounds and mucous membranes, which method and material includes the use of a material comprising certain water-insoluble hydrophilic polymers.

13 Claims, No Drawings

METHOD FOR CLEANSING FLUID DISCHARGING SKIN SURFACES, WOUNDS AND MUCOUS MEMBRANES AND MEANS FOR CARRYING OUT THE METHOD

This is a continuation of application Ser. No. 437,558, filed Jan. 27, 1974, now abandoned.

BACKGROUND

It is well known that liquid discharges from most skin wound, mucous membranes and body surfaces that have become diseased, cut or infected in one way or another. Heretofore the usual procedure has been to try to absorb such discharged liquid with some sort of a wound dressing composed of a woven or non-woven textile material that is placed over the liquid discharging skin surface.

The discharging liquid may contain, among other things, fibrinogen and fibrinogen degradation products, so called "split products". During the latter stages of blood coagulation, thrombin converts the fibrinogen enzymatically to fibrin monomers, which, due to a cross-linking reaction, promote the formation of an eschar or scab. However, the formation of such a scab on a liquid discharging skin surface is disadvantageous because the eschar forms a barrier capable of preventing the outward migration of dirt, bacteria, toxic degradation products and other substances which are detrimental to the healing process. The cleansing of the wound and subsequent healing thereof is thereby unfavourably affected.

THE PRESENT INVENTION

We decided that if the skin surface which is discharging liquid is to be kept clean (so that healing will be facilitated) it is important to have a low concentration of fibrin monomers and cross-linked fibrin immediately adjacent to the liquid discharging skin surface. We felt that the concentration of fibrin monomers and the cross-linked fibrin on the actual liquid discharging skin surface had to be so controlled that subsequent reactions, i.e. the eschar formation, do not take place directly on the liquid discharging surface itself but rather at a spaced distance therefrom. We discovered that a unique way of accomplishing this objective is to apply to the liquid discharging skin surface a mass of dry particles of a water-insoluble hydrophilic polymer capable of undergoing limited swelling to form a gel, the swellability of this polymer in water being such that the polymeric particles in a water swollen state will permit the low molecular weight constituents of blood plasma to penetrate thereinto, but which swollen particles will completely or substantially prevent the penetration of fibrinogen (having a molecular weight of about 340,000) or molecules of the size of fibrogen. The low molecular weight constituents of blood plasma which can penetrate into the swollen polymer particles would include low molecular weight salts (such as NaCl, KCl and $CaCl_2$), amino acids, urea and glucose, and also the so-called thrombocyte factors which influence the first phase of the blood coagulation process. Examples of such low molecular weight active substances include prostaglandins, serotonin, adrenaline, adenosine diphosphase (ADP), certain exo- and endotoxins having hydrolytic properties and divalent cations such as calcium or magnesium.

In accordance with one embodiment of our invention the hydrophilic polymer which we use may also be chosen so that its pores will deny penetration of the high molecular weight degradation products of the fibrinogen, for example such as those degradation products having a molecular weight of between about 270,000 and 165,000, and possibly also degradation products having a molecular weight of 85,000 and 50,000. In accordance with another embodiment of the invention, the hydrophilic polymer may be chosen so that, in addition to permitting penetration of the low molecular weight constituents of blood plasma, substances having larger molecular sizes (although smaller than fibrinogen) will be permitted to penetrate completely or partially into the water-swollen polymer (such as proteins and polypeptides, for example such having a molecular weight of approximately 5,000 or approximately 20,000 or in certain instances approximately 40,000).

The hydrophilic polymer is selected so that particles of the polymer in a water-swollen state could be used in a column for conventional gel filtration purposes, thereby enabling, by means of gel filtration techniques, the complete or partial separation of molecules of, for example, the size of fibrinogen from small or smaller molecules of the aforementioned type. The skin cleansing effect in accordance with our invention may be achieved in a particularly favourable manner by selecting polymer particles having the aforementioned properties, the water-swollen polymer comprising a three-dimensional network. The favorable results obtained in accordance with our invention appear to depend, however, on the combination of several effects. The dry hydrophilic polymer particles initially absorb liquid between the particles (which in turn depends on the radius of the particles when spherical particles are used). In addition, because of the swellability of the hydrophilic polymer particles there is thus also obtained a liquid migration in a direction from the surface of the wound through the particle layer at the same time as the swelling of the particles takes place because of contact with aqueous body fluids. Simultaneously herewith there occurs a partition chromatographic effect, since the low molecular weight constitents of the liquid are distributed both within and outside of the swollen polymer particles depending on their molecular sizes, while the larger molecules (e.g. fibrinogen), and, in accordance with some embodiments of the invention the large molecular weight split products (degradation products) are unable to penetrate the polymer particles. The substances excluded from penetrating the polymer particles migrate towards the outer boundaries of the particle mass and thus become progressively concentrated, and this takes place under slight or controllable changes in ion strength or pH. This means that the participation of the fibrinogen in the formation of a scab takes place in a zone remote from the liquid discharging skin surface, instead of directly on said surface. The content of fibrinogen split products can also be increased by means of the aforementioned concentration effect. The split products represent active components in the coagulation process, owing to the fact that they prevent the polymerization of fibrin, which leads to the formation of a defective fibrin coagulum or to no fibrin coagulum at all, and that they prevent the first phase of the blood coagulation of the fibrinogen degradation products, the so-called plasma thromboplastin formation phase. The coagulation phase, and therewith the scab formation, has in this way been modified and/or caused to stop by the formed gel and does not any longer take place directly on the discharging surface, but is moved to a zone spaced therefrom. This zone can readily be removed together with the particles, when these are removed. Cleansing of the discharging surface is facilitated by keeping the discharging surface free from such coagulation, thereby also facilitating granulation development. This greatly facilitates the later natural wound healing.

An important effect which is obtained when using the polymer particles in accordance with our invention is that bacteria (and also small particles of dirt) are entrained with the liquid departing from the discharging surface to a zone where they do not affect said surface and where they later on may be readily removed together with the gel particles. By means of such separation effects, the growth of bacteria may also be inhibited, owing to the fact that the substrate conditions for the bacteria have been changed. The gel grains also absorb nasty-smelling low molecular weight degradation products resulting from bacteria, whereby the smell from patients suffering from discharging legsores or bedsores, for example, need no longer cause the other patients and the nursing personnel as much discomfort as it presently does. Another important advantage obtained when using the polymer particles according to our invention is that the particles are soft and will not adhere to the surface of the sore, even when saturated with fluid from the discharging surface, thereby enabling the particles to be painlessly removed by means of a spatula or may be washed away with a physiological saline solution.

Some types of the dry polymer particles used in accordance with the present invention are previously known per se, for example such particles as those obtained by the cross-linking of dextran or carboxymethyl-dextran with epichlorohydrin. These particles, however, have not previously been used for cleansing discharging skin surfaces, wounds and mucous membranes in the manner which we have disclosed herein. Some of these known particles have previously been proposed to be incorporated in a water-swollen state together with other components in dermatologic compositions for other purposes. These water-swollen particles, however, do not give a cleansing effect according to the present invention, which requires that the particles be dry when applied to the surface to be treated, so that the necessary migration of fluid in the particle layer may take place.

Dermatologic compositions are known which contain different types of dry particles. Particles of polymeric substances have also been mentioned in this respect, although the particles have been of quite different types than those used in the present invention. The particularly favorable cleansing effect obtained in accordance with the present invention is not obtained with these previously known compositions containing dry particles.

In accordance with the present invention, the water-insoluble hydrophilic polymer capable of undergoing limited swelling to form a gel may contain hydroxyl groups. Thus, the product has properties which make it suitable for the present purpose, since the hydroxyl groups impart the important hydrophilic property to the polymer. The hydrophilic properties of the polymer may also be obtained by means of carboxyl groups, which may preferably be present in the form of a physiologically acceptable salt. A carboxyl group-containing polymer where the carboxyl groups may optionally be converted into salt form with, for example, a physiologically acceptable amine, may be suitable for cleansing fluid discharging skin surfaces, which, for example have arisen when the skin has got into contact with alkaline substances, such as alkali metal hydroxide.

In accordance with our invention, the polymer may contain amino groups, preferably in the form of physiologically acceptable salts, as the agent for imparting the necessary hydrophilic property to the polymer. In accordance with the invention, the polymer may also contain sulphonic acid groups, preferably in the form of physiologically acceptable salt. Such a polymer having carboxyl groups and/or sulphonic acid groups and/or amino groups may also affect the coagulation of the plasma emitted from a sore surface, thereby further delaying or preventing the formation of fibrin.

In accordance with our invention the hydrophilic property of the polymer may be such that 1 g of the dry polymer when swelling in the presence of water absorbs at least 0.5 g, and preferably at least 1 g of water. On the other hand, the swellability of the polymer should not be too high so that the polymer absorbs too much water. As mentioned above the swellability of the polymer should be such that the low molecular weight constituents of blood plasma, but not molecules of the size of fibrinogen, are able to penetrate the swellable polymer. In general, 1 g of the dry polymer absorbs less than 30 g, preferably less than 25 g, most preferably less than 20 g and for a great many applications preferably less than 15 g of water. If the gel-forming polymeric particles used in accordance with our invention comprise e.g. dextran or carboxymethyl-dextran or starch or hydroxyethyl starch cross-linked by means of epichlorohydrin in alkaline aqueous solution to a water-insoluble but swellable three-dimensional network, a particularly good result is obtained if the degree of cross-linking is such as to correspond to a water absorption ability of approximately 1.5 to 10 g and preferably approximately 2 to 5 g of water per gram of dry polymer.

In accordance with a suitable embodiment of the invention, the polymer is selected so that it has a high swelling rate when coming into contact with water or with the aqueous fluid on the skin surface to be treated. The polymeric particles should absorb water and swell at a rate which is so high that fibrin and fibrin coagulum is unable to be formed by the influence of the enzyme thrombin, etc., in the zone adjacent to the discharging surface. Since fibrin is formed at different rates with different people we deem it preferable to select a swelling rate for the particles which is sufficient for use with people having a rapid rate of fibrin formation. A good swelling rate is obtained by the presence of many hydroxyl groups in the three-dimensional network. A particularly high swelling rate is obtained by the presence of ionizable groups in the network, such as carboxyl groups, sulphonic acid groups and amino groups in salt form. As an example of a good swelling rate for this purpose caused by the presence of, for example, hydroxyl groups and/or carboxyl groups in sodium salt form and/or sulphonic acid groups in sodium salt form (in, for example, cross-linked polymers obtained by e.g. cross-linking dextran or carboxy-methyl-dextran or starch or starch derivatives with epichlorohydrin in alkaline aqueous solution) one may mention a swelling rate in physiological saline solution or in water which is such that 1 gram of the dry polymer particles absorbs in 5 seconds more than 0.02, preferably more than 0.1, most preferably more than 0.2, for example more than 0.5 g of water, and preferably less than 5, such as less than 3, e.g. less than 2 g of water.

In accordance with a particularly suitable embodiment of our invention, the water-insoluble hydrophilic polymer capable of undergoing limited swelling to form a gel comprises a three-dimensional network held together by bonds of a covalent nature.

In accordance with our invention, the polymer may comprise a hydroxyl group-containing three-dimensional network held together by bonds of a covalent nature and built up by hydroxyl group-containing polymer molecules cross-linked by means of bridges connected to said polymer molecules by ether bonds. The bridges may be straight or branched aliphatic saturated hydrocarbon chains substituted by one or more hydroxyl-groups and containing 3–20 carbon atoms, preferably 3–10 carbon atoms, said chains being optionally broken by one or more oxygen atoms. The polymeric product is insoluble, but swellable in water to form a gel, said gel in a fully water-swollen state containing more than 30%, preferably more than 50%, and most preferably more than 60% by weight of water and less than 97%, preferably less than 95%, and most preferably less than 90% by weight of water. When the polymer product contains hydroxyl-groups and/or carboxyl groups and/or sulphonic acid groups and/or amino groups, said groups may make more than 5%, preferably more than 10%, and most preferably more than 20% by weight and less than 60%, preferably less than 50%, and most preferably less than 40% by weight of the dry polymer particle. In accordance with the invention, the cross-linked polymer molecules containing the hydroxyl groups may be polymeric or polymerized carbohydrates or sugar alcohols or other polymer molecules containing hydroxyl groups. Examples of such include polymer products which are insoluble, but swellable in water obtained, for example, by cross-linking and polymerization of dextran, hydroxyethyl dextran, carboxymethyl dextran, sulphopropyl dextran, diethylaminoethyl dextran, hydroxyethyl cellulose, carboxymethyl cellulose, starch, hydroxyethyl starch, carboxymethyl starch and other polysaccharides and polysaccharide derivatives, polyvinyl alcohol, saccharose, sorbitol and mannitol in alkaline aqueous solution by means of at least bifunctional bridge forming substances of the type

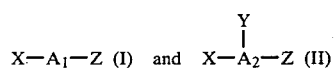

wherein X, Y and Z are each a halogen atom, preferably chloro or bromo, and $A_1$ and $A_2$ are each a straight or branched aliphatic, saturated hydrocarbon chain having one or more hydroxyl groups and preferably containing 3–20 carbon atoms, e.g. 3–10 carbon atoms, said chain being optionally broken by one or more oxygen atoms, or corresponding epoxide compounds obtainable by splitting-off hydrogen halide from the compound (I) or (II). As examples of bifunctional substances of the formula $X-A_1-Z$ and corresponding epoxide compounds capable of being obtained from $X-A_1-Z$ by splitting off hydrogen halides can be mentioned:

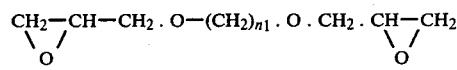

wherein $n_1$ is an integer from 2 to 4, and

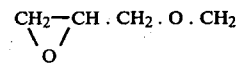

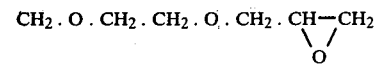

and

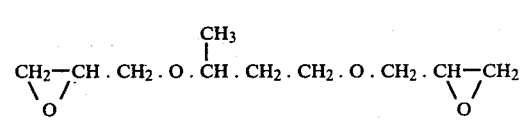

and

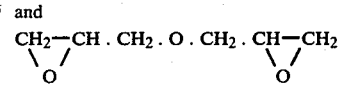

and

or corresponding halogen hydrins, and bifunctional glycerol derivatives of the formula $X-CH_2-CH(OH)-CH_2-Z$, e.g. dichlorohydrin and dibromohydrin, or corresponding epoxide compounds of the formula

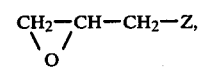

such as epichlorohydrin and epibromohydrin, obtainable by splitting off hydrogen halides. Another example of such a bifunctional compound is 1,2-3,4-diepoxybutane of the formula

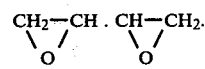

An example of trifunctional bridge forming epoxide compounds corresponding to compounds of the formula

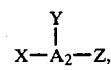

is

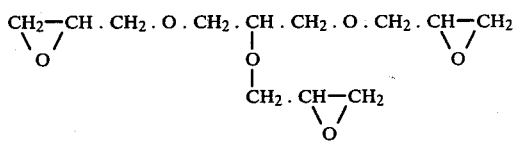

The water-soluble polymer is reacted with a sufficient quantity of a substance which is at least bifunctional to form a water-insoluble gel, i.e. a practically infinite three-dimensional network. Thus, the aforementioned water-soluble hydroxyl group-containing substances can be reacted in alkaline aqueous solution with one of the aforementioned bridge forming substances in a quantity such that a gel which is insoluble in water, but capable of undergoing swelling therein is formed by cross-linking of the polymer chains. (Diepoxides and corresponding halohydrins react, for example, with hydroxyl groups to form ether bonds.) The aforementioned bridge forming substances have also the advantage that hydroxyl groups are introduced into the bridges, thereby introducing additional hydrophilic groups into the three-dimensional network. Other hydrophilic groups can also be introduced into the hydroxyl group-containing three-dimensional network by substitution, e.g. groups containing carboxyl groups, sulphonic acid groups or amino groups or further hydroxyl groups.

In accordance with the invention, the dry polymer particles may have an average particle size within the range, for example, of 10–1000$\mu$, preferably 20–500$\mu$, most preferably 30–400$\mu$, and 50–300$\mu$ is especially desirable. The selection of the particle size depends, among other things, on the space desired between the particles. This space should preferably be selected so that the aqueous fluid rises up between the grains by capillary action. At the same time, the space should preferably be sufficiently large to allow bacteria and the like to pass between the particles. The choice of particle size may also be influenced by the facility in removing the particles from the area of application. Thus, large particles may be selected when these may be more readily removed from the discharging surface.

In accordance with the invention the polymer may be used in the form of spherical particles (e.g obtained by so-called bead polymerisation processes) or particles having irregular configuration (e.g. obtained by so-called bulk polymerisation and grinding). Examples of some polymers which can be used according to the invention provided that they present the required swelling properties are found in British patent specifications Nos. 854,715; 936,039; 974,054; and 1,013,585.

In accordance with the invention, the dry polymer particles may be applied in the form of a layer on the discharging skin surface, wound or mucous membrane surface in a manner to enable the aqueous fluid on said surface to be absorbed by the polymer, whereafter the layer of particles with fluid absorbed therein is removed from said surface. The process can be repeated one or more times until the desired degree of cleaning is obtained.

The invention also concerns a means for cleansing liquid skin, wound and mucous surfaces, said means containing, as liquid absorbing materials, dried particles of a water-insoluble hydrophilic polymer capable of undergoing limited swelling to form a gel, the swellability of the polymer in water being such that the polymeric particles in swollen state permit low molecular weight constituents, but not or only to a small degree, fibrinogen or molecules of the size of fibrinogen of blood plasma from the discharging skin surface, wound or mucous membrane to penetrate thereinto.

The polymer particles may have the same chemical composition and the same physical properties as have been stated above in connection with the claimed cleansing process.

According to one embodiment of the invention, the means may be the polymer particles alone, optionally mixed with inert fillers or other dermatologically acceptable additives such as soap, invert soap or other conventional skin cleansing agents. Perfumes, wetting agents, disinfectants, drugs or medicines may also be incorporated.

In certain cases, it may be suitable to fix the particle layer applied to a wound surface more effectively to the application site by covering the particle layer with a film of an elastic plastic material, said film having preferably small openings to admit breathing to a certain degree. When cleansing legsores it is very suitable to use such a film in the form of a "tube" surrounding the leg portion in question. The tube is then tightened below as well as above the legsore after the space between the tube and the leg being filled with the polymer particles. The protective film may also be obtained by spraying or painting a film-forming liquid dressing over the particle layer. Especially for the purpose of cleansing liquid wounds on hands and feet, the bandage may be a bag containing the dry polymer particles. The bag may, for example, be of a plastic material such as polyvinylchloride or of fabrics.

According to a further embodiment of the invention, the polymer particles are mixed with or incorporated in different inert materials to provide dressings or bandages, for example. The polymer particles may thus be mixed in dry or wet condition with different fiber materials. Suitable fiber materials are, for example, cellulose fibers or paper pulp. Cotton fibers, the length of which can be varied to suitable dimensions, may also be mixed with the polymer particles. The weight proportion between polymer particles and fiber material can be varied within broad limits such as between 5:1 and 1:5. If the polymer particles are mixed in wet condition with the fiber materials, the obtained wet mass is preferably formed to a sheet and the sheet is then dried.

The polymer particles and any additives such as fibers can also be mixed with dermatologically acceptable binders such as polyethylene glycols, carboxymethyl cellulose or gummi arabicum. These binders are preferably selected so that the mixture obtained will get a consistency and adherence suitable for administration on the body surface, whereby the particle layer remains on the surface. The mixture may suitably have the form of an ointment. If necessary this consistency may be obtained by mixing the particles with different binders, such as polyethylene glycols having different molecular weights.

According to a further embodiment of the invention, the polymer particles, optionally with additives, may be enclosed between thin layers of paper, fabric of cotton or inert plastics. In this connection, the fabric shall, of course, present such a mesh size that the polymer particles should not pass through the meshes. Instead of fabrics thin films of tissue-acceptable plastics such as polyethylene, polypropylene and polyvinylchloride may be used said films being capable, optionally through small openings, of admitting passage of liquids and gases. Such bandages having the polymer particles enclosed between layers of different materials, are suitably divided into a plurality of small sections, for example, in the form of a diamond pattern, to impart a higher rigidity to the bandage. The two films enclosing polymer particles can be of the same material or different materials. In addition to the particles, the bandages may comprise such dermatologically acceptable additives as discussed above in connection with the particles. The polymer particles may also be incorporated in different porous foamy tissue-acceptable materials, such as gelatine foam etc.

In many cases, it is suitable that the means is sterile. This can be attained in different ways, for example, by heat sterilization, sterilization by gamma irradiation or by treatment with agents capable of killing microorganisms.

In accordance with the invention, a polymeric product capable of being slowly broken down enzymatically to water-soluble fragments may also be used. In this respect, it is possible to use starch, hydroxyethyl starch or carboxymethyl starch or other starch derivatives which has been cross-linked in the afore-mentioned manner by a bridge forming agent which is at least bifunctional, the degree of total substitution for the starch being selected so that α-amylase is able to break glucosidic linkages in the three-dimensional network to a sufficient extent, so that the polymer gel particles gradually disappear as water-soluble fragments as a result of the influence of α-amylase in the aqueous body fluid, if the particles should not have been removed after the cleansing process.

The invention will now be illustrated by means of a number of working examples, which, however, are not intended to limit the scope of the invention.

EXAMPLE 1

Following an operation, a twenty-seven year old woman developed a large (5×5 cm) infected sore on her left foot. The sore discharged a nasty-smelling liquid. Bacteriological tests showed a pronounced growth of S. aureus. For the purpose of cleansing the sore, there was applied directly thereto a layer of dry water-insoluble particles of dextran cross-linked with epichlorohydrin (the reaction having been effected in alkaline aqueous solution, cf. British Pat. No. 974,054) having a swellability of 2.5 g of water per g of dry substance in a quantity of 1 g of sterile dry particles per 5 cm² of sore surface. The average particle size was approximately 200μ. The sore with the cross-linked dextran particles applied thereon was covered with a sterile gauze bandage. The layer of particles was examined after 6 hours and it was found that the particles had converted to a slightly yellow gel containing discharged fluid, absorbed from the sore. The particles had no smell. The gel particles were removed from the bed of the sore by means of a plastic spatula. Remaining gel particles were washed from the sore with physiological saline solution. The treatment was repeated at 12 hours intervals. After 24 hours the sore was found to be clinically clean. No signs of infection could be clinically observed. The sore presented a healthy granulation surface at its bottom and was odourless. Cultures from the sore showed a very slight growth of S. aureus. After 2 days, no bacteria could be found. The test was repeated for 5 days, without any complications being observed. As the sore dried up, the quantity of particle mass required, decreased progressively. On the 5th day, the sore was found to be 4.5×4.5 cm in size. On the sixth day the epitel defect was covered with a pork-skin graft, which healed without difficulty and within a normal time period.

EXAMPLE 2

An 83 year old woman had suffered for 20 years from venous circulation insufficiently in the legs. For 10 years she had an infected, painful sore on her left lower leg. The sore was 10×15 cm in size and discharged a nasty-smelling fluid. Previous attempts to cleanse the sore had been in vain. Surgical treatment could not be contemplated because of the poor general condition of the woman. For the purpose of cleansing the surface of the sore, there was applied directly thereto a layer of dry sterile water-insoluble particles of cross-linked dextran (cross-linked with epichlorohydrin in alkaline aqueous solution, cf. British Pat. No. 974,054) having a swellability of 5 g of water per g of dry particles and an average particle size of approximately 200μ, in a quantity of 1.5 g per 5 cm² of sore surface. After 12 hours, the gel which had formed was washed away from the area of the sore with 0.9% saline solution. The treatment was repeated at 12 hours intervals. After being thus treated for three days, the sore was clinically pure with healthy granulations and no sign of infection. The sore was odourless and much less painful than before the treatment.

EXAMPLE 3

A man 20 years of age, after having a tooth extracted from the lower jaw, developed a pocket-like, mucous membrane defect, 5×10×5 mm, which showed no tendency towards spontaneous healing despite repeated and careful hygiene for two weeks. Surrounding mucous membrane was red and swollen. For the purpose of cleansing the cavity-like sore, the cavity was filled with dry sterile water-insoluble particles of carboxymethyl dextran in the form of sodium salt cross-linked with epichlorohydrin (cf. British Pat. No. 1,013,585). The total swellability per gram was more than 2 and less than 10 g of water. The swelling rate of the dry particles in physiological saline solution was 0.7 g per g/5 sec., and the average particle size was approximately 80μ. The gel formed in the cavity was washed away at 12 hours intervals and replaced with dry particles. After two days the cavity was found to be clean and its size reduced by half. Surrounding mucous membrane was no longer red or swollen. The sore healed spontaneously after a further two days.

EXAMPLE 4

A man, 50 years of age, had suffered for five years from bad circulation in the left lower leg, as a result of constrictions in the leg artery, and had suffered for one month from an infected and extremely painful sore on his left toe. The sore was one inch in diameter and emitted a discharge. Using the same technique as that described with reference to Example 1, the surface of the sore was covered with water-insoluble spherical sterile particles of diethylaminoethyl dextran, cross-linked with epichlorohydrin (cf. British Pat. No. 1,013,585). The particle size was approximately 80μ. The total swellability per g of the polymer was more than 2 and less than 10 g of water. The swelling rate of the dry particles in physiological sodium chloride solution was 0.4 g per g/5 sec. After three calendar days, the sore was found to be completely dry and no discharge was manifest. Neither could any signs of infection be determined clinically. The pain experienced by the patient progressively decreased during the treatment period.

EXAMPLE 5

A 2 year old boy was inadvertently scalded with boiling water on his chest over an area corresponding to twice the size of the palm of an adult hand. After three hours serious blisters were observed to have formed on the area of the burn. The blisters were punctured and the burned surface covered with a layer of dry spherical particles consisting of cross-linked starch. The particle layer was covered with a thin foil of PVC Plastic ("Gladpack", Union, Union Carbide). The mass of swollen gel particles formed by the secretion from the sore was washed away four times a day. A fresh layer of the same spherical particles consisting of cross-linked starch were applied to the burned area together with the PVC foil after each washing operation. The boy suffered no pain whatsoever either during the treatment process or when the bandages were changed. The burns healed without complication in seven days, without the formation of a scab and without sign of infection. The treated area remained pale during the whole treatment period and showed no signs of swelling.

The spherical cross-linked starch particles which were used in this treatment were obtained by a dispersion polymerization technique in accordance with the disclosures of British Pat. No. 974,054, according to which ethylene dichloride is used as coherent phase in the dispersion and epichlorohydrin as a cross-linking agent. From the spherical particles thus produced, a particle fraction having an average diameter of approximately 100μ in dry state was removed by sieving. The water absorption capacity was approximately 4.5 g of water per one gram of dry cross-linked starch. The particles were sterilized by γ-radiation.

The particles dissolved completely with long duration influence of α-amylase in neutral aqueous solution.

EXAMPLE 6

A 25 year old man, totally lame from the navel downwards, had suffered a pressure sore on his right side as a result of his invalidity and his impaired sense of touch. Over a period of two months, the sore had progressively deepened and secondary infection had set in, despite intensive treatment with antibiotics applied both locally and parenterally. Relatively large quantities of debris were daily rejected from the sore cavity. The sore cavity, which had a capacity of 25 ml, was filled with particulate material consisting of dextran cross-linked with epichlorohydrin, average particle size approximately 200μ swellability 2.5 g/g of water per gram dry substance, the particles being mixed with finely ground bleached cellulose in the ratio particles/cellulose wadding of 3:1. Over a period of six hours a fully swollen particle mass formed which could readily be removed from the sore cavity by washing the same with a 0.9% solution of sodium chloride in water. The treatment was repeated four times a day, and after two days it was observed that the sore cavity was perfectly clean with healthy granulations at the bottom thereof and progressively decreasing secretion therefrom. The patient was treated in this manner for five days, whereafter the sore cavity was plugged with sodium chloride wads which were changed once a day. The pressure sore healed spontaneously twelve days later.

EXAMPLE 7

Particles produced in accordance with our invention were incorporated to advantage in inert materials having little or no chromatographic effect in an aqueous environment, e.g. fine paper pulp, cotton fabric and macroporous plastics. In this way we produced readily handled, flexible and soft bandages or dressings that could be readily applied to discharging and weeping skin surfaces for the purpose of cleaning the same, and which could also be readily removed.

A dressing of this nature was produced in the following manner:

4 Parts by weight of dry spherical particles consisting of dextran cross-linked with epichlorohydrin in alkaline aqueous solution and having a swellability of 2.5 grams of water per gram of dry substance were added under agitation to 2 g of bleached fine paper pulp suspended in water. The mixture was stirred strongly with a magnet agitator for 30 minutes, whereafter the mixture was applied to a Buchner-funnel to which was connected a zone of pressure below ambient pressure for 12 hours. A dressing was obtained which could readily be removed from the glass surfaces and which could be subsequently dried in a heating cabinet at 60° C. for 12 hours. The dressing was examined under a microscope. It was observed that the fibres of the paper pulp had been uniformly distributed between the sperhical particles. Thus, a flexible, soft, light elastic material was obtained from which pieces could be readily punched, cut or clipped to the desired size. The dressing was also found to possess good tensile strength properties, which could be further enhanced by intermixing an inert binder. In a similar manner, an agent was prepared with the following mixing ratios: 3 g paper pulp/3 g polyer; 4 g pulp/2 g polymer; 4 g pulp/1 g polymer; 2 g pulp/4 g polymer; and 1 g pulp/4 g polymer. Upon saturating the dry dressing with water, a mass possessing suitable chromatographic properties was obtained. It was possible to show the properties in the following manner. To a dry dressing produced in accordance with the above and admixed with 25% by weight of fine paper pulp there was added 25 μl of an albumin glycine solution. The same was absorbed in the dressing immediately, and at the same place as the sample was applied, 4 ml of a physiological acceptable sodium chloride solution was pipetted immediately thereafter. As the dressing converted to gel form, the albunin was separated from the low molecular weight glycine which latter was able to penetrate the three-dimensional network of the particles. Upon subsequent colouring it could be established that the albumin fraction had been separated from the glycine centripetally. A dry dressing produced in accordance with the above (containing a paper pulp to polymer weight ratio of 1:3) was applied by means of surgical tape to a dirty, infected and weeping sore. The sore had appeared one week previously due to a skin burn and secondary infection had set in. The secondary infection was serious and the sore painful. The dressing was changed four times a day for two days, whereafter it could be observed that the surface of the sore was perfectly clean with healthy granulation development. The sore was painless and less discharge was observed. The sore could then be transplanted, and the transplant healed without being rejected. The patient experienced no pain when the dressings were changed.

EXAMPLE 8

A woman, 22 years of age, suffered from a trophic sore—approximately one half-inch in size—on the sole of her left foot. The sore had developed as a result of reduced sensibility in the whole leg after a traffic accident two years earlier.

The sore had been treated for one year with saline compresses changed at close intervals and with alternating treatment with trypsin and Burows solution, without the sore becoming sufficiently clear to enable secondary suture or skin grafts to be made. For the purpose of cleaning the sore, there were used dry particles of cross-linked dextran (cross-linked with epichlorohydrin in alkaline aqueous solution, cf. British Pat. No.

974,054). The polymer product was insoluble in water but capable of undergoing swelling therein, 1 g of dry product absorbing 2.5 g of water.

The average particle size was approximately 100μ. The polymeric particles were applied directly to the sore, 2 g of particles being used per cm² of the sore surface. The particle mass was removed after 6 hours. The dry particles were found to have swollen to form water-containing gel particles and the surface of the sore was found to be much cleaner. Prior to the treatment the sore presented gray, devitalised areas with bacteria infection at the bottom thereof. Already after 6 hours the surface was healthier and had a higher degree of redness, and after 24 hours of treatment the sore was perfectly clean and bacteriological tests showed no bacteria present.

EXAMPLE 9

The cleansing method and means of the present invention was tested on a 20 year old man suffering from discharging eczema in both groins. The condition had been chronic for one year, among other things because of the pronounced stoutness of the patient. The state of the sore was troublesome owing to pain and constant secretion.

A dry sterile powder in the form of spherical particles of cross-linked dextran (cross-linked with epichlorohydrin in alkaline aqueous solution, cf. British Pat. No. 974,054) was applied over the whole of the eczeme area. The average particle size of the powder was approximately 400μ. The swellability in water was 2.5 g of water per g of dry polymer product. The sore was left uncovered during the whole of the treatment process. After 6 hours it was seen that the particles in the region of the eczema had converted to water-containing gel grains. The gel became saturated 12 hours later, whereupon it was washed away.

The exzema infected surface was found to be clean and dry and less irritated, and no crust formation was found on the surface. The patient suffered less pain. The surface of the skin was still dry 12 hours after the gel had been removed.

In a manner similar to that described in the above examples, usable dry particles of other polymeric products having the given properties can be obtained e.g. by cross-linking dextran, carboxymethyl dextran (the carboxyl groups being in the form of Na-salt), 3-sulphopropyl dextran (in the form of Na-salt), diethylaminoethyl dextran (in the form of HCl-salt) or starch or hydroxyethyl starch or carboxymethyl starch with 1,4-butanedioldiglycide ether or other diepoxides.

The products substituted with ionizable groups showed a noticable rapid swelling.

EXAMPLE 10

An ointment was made up from the following ingredients:

| | | |
|---|---|---|
| (a) | Polyethyleneglycol having an average molecular weight of about 300 (Macrogol 300) | 14.3% |
| (b) | Polyethyleneglycol having an average molecular weight of about 1500 (Macrogol 1540) | 28.6% |
| (c) | Dry particles of cross-linked dextran having an average particle size of about 200 um and a swellability in water of 2.5 g of water per gram of dry substance (prepared according to the British Patent No. 974,054) by cross-linking dextran with epichlorohydrin in alkaline solution) | 57.1% |
| | | 100.0% by weight |

This ointment is useful for application to fluid discharging wound surfaces, wounds and mucous membranes.

The disclosure of the patents mentioned earlier in this specification are incorporated herein by reference.

A certified copy of our Swedish application No. 73011 97-5, filed Jan. 29, 1973, is attached hereto and it is requested that the right of priority provided by 35 U.S. Code 119 be extended by the Patent Office. The disclosure of this Swedish application is incorporated herein by reference.

We claim:

1. A method for cleansing an infected sore which method comprises applying thereto an effective amount of spherical dry polymer particles within the size range of 20 to 500μ, said polymer particles consisting of dextran cross-linked with epichlorohydrin so as to form a three-dimensional network held together by bonds of covalent nature, one gram of which swells in the presence of water to absorb at least 0.5 grams of water but less than 15 grams of water, the swellability of the polymer particles in water being such that the polymeric particles in swollen state have a pore size which permits the penetration thereinto of low molecular weight materials discharging from the sore but which completely or substantially excludes penetration thereinto of materials discharging from the sore that have a molecular weight greater than about 50,000.

2. A method for cleansing an infected sore which method comprises applying thereto an effective amount of spherical dry particles within the size range of 20 to 500μ, said particles consisting of a hydrophilic hydroxyl-group-containing polymer comprising polymeric or polymerized carbohydrates or sugar alcohols cross-linked to a three-dimensional network held together by bonds of covalent nature which polymer is water-insoluble but has a swellability in water such that the polymeric particles in swollen state permit penetration thereinto of low molecular weight materials discharging from the sore, but completely or substantially exclude penetration thereinto of fibrinogen and its high molecular weight degradation products from the sore having a molecular weight greater than 50,000.

3. A method according to claim 2 wherein the polymer contains carboxyl groups, preferably in salt form.

4. A method according to claim 2 wherein the polymer contains sulphonic acid groups, preferably in salt form.

5. A method according to claim 2 wherein the polymer contains amino groups, preferably in salt form.

6. A method according to claim 2 wherein the polymer is so hydrophilic that one gram of the dry polymer, when swelling in the presence of water, absorbs at least 0.5 grams of water.

7. A method according to claim 2 wherein the polymer is cross-linked by means of bridges comprising straight or branched aliphatic saturated hydrocarbon chains bound to said polymeric or polymerized carbohydrates or sugar alcohols by ether linkages said hydrocarbon chains containing 3–20 carbon atoms, and being substituted by at least one hydroxyl group and being optionally broken by one to three oxygen atoms, and wherein the polymer in fully water-swollen state contains more than 40% by weight of water.

8. A method according to claim 2 wherein the polymer is applied to the sore to be cleansed in the form of a layer so that the material discharging from the sore is absorbed by the polymer, the polymer layer together with absorbed material therein being removed from the sore and the treatment repeated until the desired degree of cleanness has been obtained.

9. A method for cleansing an infected sore which method comprises applying thereto an effective amount of dry polymer particles comprising a polysaccharide polymer cross-linked to a three-dimensional network held together by bonds of covalent nature which cross-linked polymer is water-insoluble but has a swellability in water such that the particles in swollen state permit penetration thereinto of low molecular weight constituents, and completely or substantially exclude penetration thereinto of fibrinogen or molecules of the size of fibrinogen of blood plasma from the sore.

10. A method according to claim 9 wherein the polysaccharide polymer is dextran.

11. A method according to claim 9 wherein the polysaccharide polymer is starch.

12. A method according to claim 9 wherein the polysaccharide polymer is dextran cross-linked with epichlorohydrin.

13. A method for cleansing an open infected sore which comprises establishing upon the infected sore a gel chromatographic zone so that the various molecular weight components of the aqueous fluids exuding from the sore will migrate away from the surface of the sore and through said gel chromatographic zone to different degrees, depending on their molecular weights, said gel chromatographic zone being established by depositing upon the infected sore a particulate mass comprising dry particles, each of said particles:
(a) consisting of a water-insoluble hydroxyl-group containing polymer, comprising polymeric or polymerized carbohydrates or sugar alcohols cross-linked to a three-dimensional network held together by bonds of covalent nature,
(b) being capable of undergoing at least limited swelling to form a gel when contacted with the aqueous fluids which exude from the infected sore, one gram of said polymer particles being able to swell in the presence of water to absorb at least 0.5 grams of water but less than 15 grams of water,
(c) being within the size range of 20 to 500$\mu$,
(d) being spherical in shape,
(e) having a pore size in a swollen state
 (1) that permits penetration thereinto of low molecular weight materials discharging from the sore but
 (2) that completely or substantially excludes penetration thereinto of materials discharging from the sore that have a molecular weight greater than 50,000 whereby
by virtue of the gel chromatographic effect obtained by absorbtion and migration of the aqueous fluids exuding from the sore eschar formation is prevented directly on the liquid discharging surface of the infected sore,
bacteria are entrained in the components migrating from the discharging surface of the sore to a zone spaced therefrom where they do not affect the surface of the sore and where they later on may be readily removed together with the gel particles, and
the soft swollen polymer particles may be painlessly removed when desired.

* * * * *

UNITED STATES PATENT AND TRADEMARK OFFICE
CERTIFICATE OF CORRECTION

PATENT NO. : 4,225,580

DATED : September 30, 1980

INVENTOR(S) : Rothman et al.

It is certified that error appears in the above—identified patent and that said Letters Patent is hereby corrected as shown below:

On the title page, add Item [30] to read:

--- Sweden [SE]   7301197-5   Jan. 29, 1973 ---.

Signed and Sealed this

Twenty-eighth Day of July 1981

[SEAL]

Attest:

Attesting Officer

GERALD J. MOSSINGHOFF

Commissioner of Patents and Trademarks

REEXAMINATION CERTIFICATE (261st)
United States Patent [19]
Rothman et al.

[11] B1 4,225,580
[45] Certificate Issued Oct. 9, 1984

[54] METHOD FOR CLEANSING FLUID DISCHARGING SKIN SURFACES, WOUNDS AND MUCOUS MEMBRANES AND MEANS FOR CARRYING OUT THE METHOD

[75] Inventors: Ulf S. E. Rothman, Bjärred; Sten A. L. Jacobsson, Malmö, both of Sweden

[73] Assignee: Pharmacia Aktiebolag, Uppsala, Sweden

Reexamination Request:
No. 90/000,113, Nov. 20, 1981

Reexamination Certificate for:
Patent No.: 4,225,580
Issued: Sep. 30, 1980
Appl. No.: 619,148
Filed: Oct. 2, 1975

Certificate of Correction issued Jul. 28, 1981.

Related U.S. Application Data

[63] Continuation of Ser. No. 437,558, Jan. 27, 1974, abandoned.

[51] Int. Cl.³ .................... A61K 31/74; A61K 31/70
[52] U.S. Cl. ......................................... 424/78; 424/180
[58] Field of Search ................................. 424/78, 180

[56] References Cited

U.S. PATENT DOCUMENTS

| | | | |
|---|---|---|---|
| 2,626,257 | 1/1953 | Caldwell et al. | 260/233.3 |
| 2,684,321 | 7/1954 | Thurmon et al. | 167/58 |
| 2,857,311 | 10/1958 | Thurmon et al. | 167/58 |
| 2,951,012 | 8/1960 | Gisvold | 167/58 |
| 3,002,823 | 10/1961 | Flodin | 23/293 |
| 3,589,364 | 6/1971 | Dean | 128/284 |
| 3,624,209 | 11/1971 | Granatek | 424/157 |
| 3,669,103 | 6/1972 | Harper et al. | 128/156 |
| 3,670,731 | 6/1972 | Harmon | 128/284 |
| 3,810,468 | 5/1974 | Harper et al. | 128/156 |
| 3,922,342 | 11/1975 | Rathbun | 424/79 |

FOREIGN PATENT DOCUMENTS

| | | |
|---|---|---|
| 854715 | 11/1960 | United Kingdom . |
| 936039 | 9/1963 | United Kingdom . |
| 974054 | 11/1964 | United Kingdom . |
| 1013585 | 12/1965 | United Kingdom . |
| 1192581 | 5/1970 | United Kingdom . |
| 1200106 | 7/1970 | United Kingdom . |
| 1454055 | 10/1976 | United Kingdom . |

OTHER PUBLICATIONS

"Gelchromatography"–Determann, (1967), pp. 26-31, Materials and Methods, pub. by Springer-Verlag, New York, (1967).
"Pharmacopea Nordica", pub. by Apotekarsocietetens Förlag Stockholm, 1964, pp. 80 and 81.
U.S. Pat. application No. 21,312, filed 4/15/48, parent of U.S. Pat. No. 2,626,257.
Fass, "The Index of Pharmaceutical Specialties in Sweden", (1972); p. 379 and partial translation.
Label from package of commercial "Bio-Sorb" Dusting Powder.
"Sephadex" Ion Exchangers, Pharmacia Fine Chemicals, Pharmacia Aktiebolag, (1973), pp. 8-11.
The Pharmacological Basis of Therapeutics, (1970).
The Pharmacological Basis of Therapeutics, (1980), p. 953.
Swedish Patent Office action dated Jan. 27, 1982 relating to Swedish Patent application 7301197-5 & partial translation.
Office action and translation from German Patent application, P2403269, 7-41 & translation of Claim 1.
Webster's Medical Dictionary published by Ottenheimer Pub. Inc., Copyright 1977, p. 246.
Principles of Internal Medicine, Eighth Edition by Adams et al., MacGraw-Hill, Tokyo, Japan, (1977), pp. 790 and 1507.
The Swedish medical periodical Laekartidninger No. 37, (1980), pp. 3078-3079 and translation.
Responses filed by Patent Owner to the Swedish and Norwegian Patent Office actions in patent cases equivalent to U.S. Pat. No. 4,225,580.
The Extra Pharmacopoea by Martindale, (1972), pp. 574 & 1392.
Annals of Surgery, vol. 151, No. 1, (Jan. '60), pp. 106-112.

*Primary Examiner*—Frederick E. Waddell

[57] ABSTRACT

The present invention relates to a method and material for cleansing fluid discharging skin surfaces, wounds and mucous membranes, which method and material includes the use of a material comprising certain water-insoluble hydrophilic polymers.

REEXAMINATION CERTIFICATE ISSUED UNDER 35 U.S.C. 307.

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-13 is confirmed.

New claims 14-52 are added and determined to be patentable.

*14. A method for cleansing a fluid-discharging infected sore located on the exterior of the body which method comprises applying to the sore a particulate mass of spherical dry water-insoluble polymer particles within the size range of 30 to 400μ, said polymer particles consisting of dextran cross-linked with epichlorohydrin so as to form a three-dimensional network held together by bonds of covalent nature, one gram of which swells in the presence of water to absorb at least 1 gram of water but less than 15 grams of water, the swellability of the polymer particles in water being such that the polymeric particles in swollen state have a pore size which permits the penetration thereinto of low molecular weight materials discharging from the sore but which substantially excludes penetration thereinto of materials discharging from the sore that have a molecular weight greater than 50,000, which excluded materials migrate between the particles towards the outer boundaries of the particulate mass, thereby avoiding formation of a scab directly on the surface of the infected sore, and maintaining said particulate mass in contact with said sore for a sufficient length of time to permit penetration into the particles of low molecular weight materials discharging from the sore and thereafter removing the resulting particulate mass from contact with said sore.*

*15. A method for cleansing a fluid-discharging infected sore located on the exterior of the body which method comprises applying to the sore a particulate mass of spherical dry polymer water-insoluble particles within the size range of 30 to 400μ, said particles consisting of a hydrophilic hydroxyl-group-containing polymer comprising polymeric or polymerized carbohydrates or sugar alcohols cross-linked into a three-dimensional network held together by bonds of covalent nature, one gram of which polymer swells in the presence of water to absorb at least 1 gram of water but less than 15 grams of water, the swellability in water being such that the polymeric particles in swollen state permit penetration thereinto of low molecular weight materials discharging from the sore, but substantially exclude penetration thereinto of fibrinogen and degradation products from the sore having a molecular weight greater than 50,000, which excluded materials migrate between the particles towards the outer boundaries of the particulate mass, thereby avoiding formation of a scab directly on the surface of the infected sore, and maintaining said particulate mass in contact with said sore for a sufficient length of time to permit penetration into the particles of low molecular weight materials discharging from the sore and thereafter removing the resulting particulate mass from contact with said sore.*

*16. A method according to claim 15 wherein said polymer particles are selected from water-soluble dextran, starch, and derivatives thereof being cross-linked in aqueous solution to form a water-insoluble three-dimensional network held together by bonds of covalent nature, one gram of which swells in the presence of water to absorb approximately 1.5 to 10 grams of water.*

*17. A method according to claim 15 or claim 16 wherein one gram of said polymer particles will swell in water to absorb 2 to 5 grams of water.*

*18. A method according to claim 16 wherein said polymer particles have a size within the range of 50-300μ.*

*19. A method according to claim 15 wherein the polymer is cross-linked by means of bridges comprising straight or branched aliphatic saturated hydrocarbon chains bound to said polymeric or polymerized carbohydrates or sugar alcohols by ether linkages, said hydrocarbon chains containing 3-20 carbon atoms, and being substituted by at least one hydroxyl group and being optionally broken by one to three oxygen atoms, and wherein the polymer in fully water-swollen state contains more than 50% by weight of water.*

*20. A method according to claim 19 wherein the polymer in the fully water-swollen state contains more than 60% by weight of water and less than 90% by weight of water.*

*21. A method for cleansing a fluid-discharging infected sore located on the exterior of the body which method comprises applying to the sore a particulate mass of dry water-insoluble polymer particles having a size range of 30-400μ comprising a polysaccharide polymer cross-linked into a three-dimensional network held together by bonds of covalent nature, one gram of which polymer swells in the presence of water to absorb at least 1 gram of water but less than 15 grams of water, the swellability in water being such that the particles in swollen state permit penetration thereinto of low molecular weight constituents, and substantially exclude penetration therein of fibrinogen or molecules of the size of fibrinogen of blood plasma from the sore, and maintaining said particulate mass in contact with said sore for a sufficient length of time to permit penetration into the particles of low molecular weight materials discharging from the sore and thereafter removing said particulate mass from contact with said sore.*

*22. A method according to claim 21 wherein said polymer particles are spherical.*

*23. The method according to claim 21 wherein the particles have a size range of 50-300μ.*

*24. The method according to claim 21 wherein said polysaccharide polymer is selected from water-soluble dextran, starch and derivatives thereof which are cross-linked in aqueous solution to form a water-insoluble three-dimensional network held together by bonds of covalent nature, one gram of which swells in the presence of water to absorb approximately 1.5 to 10 grams of water.*

*25. The method according to claim 24 wherein the particles have a size of 50-300μ.*

*26. The method of any one of claims 21-25 wherein the polymer is cross-linked by means of bridges comprising straight or branched aliphatic saturated hydrocarbon chains bound to said polysaccharide polymer by ether linkages, said hydrocarbon chains containing 3-20 carbon atoms and being substituted by at least one hydroxyl group and being optionally broken by one to three oxygen atoms, and wherein the polymer in fully water-swollen state contains more than 60% by weight of water and less than 90% by weight of water.*

27. A method according to any one of claims 21-25 wherein the polysaccharide polymer is dextran.

28. A method according to any one of claims 21-25 wherein the polysaccharide polymer is starch.

29. A method according to any one of claims 21-25 wherein the polysaccharide polymer is dextran cross-linked with epichlorohydrin.

30. A method for cleansing a fluid-discharging infected sore located on the exterior of the body which method comprises establishing upon the surface of the sore a gel chromatographic zone so that the various molecular weight components of the fluids exuding from the sore will migrate away from the surface of the sore and through said gel chromatographic zone to different degrees, depending on their molecular weights, said gel chromatographic zone being established by depositing upon the surface of the sore a particulate mass comprising dry water-insoluble polymer particles, each of said polymer particles:

(a) consisting of a water-insoluble hydroxyl-group containing polymer, comprising polymeric or polymerized carbohydrates or sugar alcohols cross-linked into a three-dimensional network held together by bonds of covalent nature, (b) being capable of undergoing at least limited swelling to form a gel when contacted with the aqueous fluids which exude from the sore, one gram of said polymer particles being able to swell in the presence of water to absorb at least 1 gram of water but less than 15 grams of water, (c) being within the size range of 30 to 400μ, (d) being spherical in shape, (e) having a pore size in a swollen state
  (1) that permits penetration thereinto of low molecular weight materials discharging from the sore but
  (2) that substantially excludes penetration thereinto of materials discharging from the sore that have a molecular weight greater than 50,000, which excluded materials migrate between the particles towards the outer boundaries of the particulate mass, maintaining said particulate mass in contact with said sore for a sufficient length of time to permit penetration into the particles of low molecular weight materials discharging from the sore and thereafter removing the resulting particulate mass from contact with said sore whereby, by virtue of the gel chromatographic effect obtained by absorption and migration of the fluid exuding from the sore, eschar formation is prevented on the liquid discharging surface of the sore, and bacteria are entrained in the components migrating from the discharging surface of the sore to a zone spaced therefrom where they do not affect the surface of the sore and where they later on may be readily removed together with the gel particles.

31. A method according to claim 30 wherein the polymer particles are selected from water-soluble dextran, starch, and derivatives thereof being cross-linked in aqueous solution to form a water-insoluble three-dimensional network held together by bonds of covalent nature one gram of which swells in the presence of water to absorb approximately 1.5 to 10 grams of water.

32. A method according to claim 31 wherein one gram of said polymer particles will swell in water to absorb 2 to 5 grams of water.

33. A method according to claim 31 wherein said polymer particles have a size within the range of 50-300μ.

34. A cleansing method according to any one of claims 15-20 or 30-33 wherein said carbohydrate polymer is dextran.

35. A cleansing method according to any one of claims 15-20 or 30-33 wherein said carbohydrate polymer is starch.

36. A cleansing method according to any one of claims 15-20 or 30-33 wherein said carbohydrate polymer is a starch derivative.

37. A cleansing method according to claim 34 wherein the polymer is cross-linked by means of bridges comprising straight or branched aliphatic saturated hydrocarbon chains bound to said polymeric or polymerized carbohydrates or sugar alcohols by ether linkages, said hydrocarbon chains containing 3-20 carbon atoms, and being substituted by at least one hydroxyl group and being optionally broken by one to three oxygen atoms, and wherein the polymer in fully water-swollen state contains more than 50% by weight of water.

38. A cleansing method according to claim 35 wherein the polymer is cross-linked by means of bridges comprising straight or branched aliphatic saturated hydrocarbon chains bound to said polymeric or polymerized carbohydrates or sugar alcohols by ether linkages, said hydrocarbon chains containing 3-20 carbon atoms, and being substituted by at least one hydroxyl group and being optionally broken by one to three oxygen atoms, and wherein the polymer in fully water-swollen state contains more than 50% by weight of water.

39. A cleansing method according to any one of claims 16-18 and 27-33 wherein said polymer is cross-linked by means of bridges comprising straight or branched aliphatic saturated hydrocarbon chains bound to said polymeric or polymerized carbohydrates or sugar alcohols by ether linkages, said hydrocarbon chains containing 3-20 carbon atoms, and being substituted by at least one hydroxyl group and being optionally broken by one to three oxygen atoms, and whereby the polymer in fully water-swollen state contains more than 50% by weight of water.

40. A cleansing method according to any one of claims 15-25 and 30-33 wherein said polymer to be cross-linked is selected from the group consisting of hydroxyl ethyl dextran, carboxy methyl dextran, sulphopropyl dextran, diethylamino ethyl dextran, starch, hydroxyethyl starch or carboxy methyl starch.

41. A cleansing method according to any one of claims 14-25 wherein said application of polymers is directly upon said infected sore.

42. A cleansing method according to claim 26 wherein said application of polymers is directly upon said infected sore.

43. A cleansing method according to claim 27 wherein said application of polymers is directly upon said infected sore.

44. A cleansing method according to claim 28 wherein said application of polymers is directly upon said infected sore.

45. A cleansing method according to claim 29 wherein said application of polymers is directly upon said infected sore.

46. A cleansing method according to any one of claims 30-33 wherein said application of polymers is directly upon said infected sore.

47. A cleansing method according to claim 34 wherein said application of polymers is directly upon said infected sore.

48. A cleansing method according to claim 35 wherein said application of polymers is directly upon said infected sore.

49. A cleansing method according to claim 36 wherein said application of polymers is directly upon said infected sore.

50. A cleansing method according to claim 37 wherein said application of polymers is directly upon said infected sore.

51. A cleansing method according to claim 38 wherein said application of polymers is directly upon said infected sore.

52. A cleansing method according to claim 39 wherein said application of polymers is directly upon said infected sore.

* * * * *